United States Patent [19]

Colton et al.

[11] Patent Number: 5,372,930

[45] Date of Patent: Dec. 13, 1994

[54] SENSOR FOR ULTRA-LOW CONCENTRATION MOLECULAR RECOGNITION

[75] Inventors: Richard J. Colton, Springfield; David A. Kidwell, Alexandria, both of Va.

[73] Assignee: The United States of America as represented by the Secretary of the Navy, Washington, D.C.

[21] Appl. No.: 945,057

[22] Filed: Sep. 16, 1992

[51] Int. Cl.$^5$ .......................................... G01N 33/543
[52] U.S. Cl. ........................................ 435/6; 250/306; 250/307; 422/50; 422/68.1; 435/7.1; 435/291; 436/501; 436/518; 436/524; 436/525; 436/527; 436/531; 436/532
[58] Field of Search .................. 250/306, 307; 422/50, 422/68.1; 435/6, 7.1, 291; 436/501, 518, 524, 525, 527, 531, 532

[56] References Cited

U.S. PATENT DOCUMENTS 5,047,633  9/1991  Finlan et al. ........................ 250/307
5,106,729  4/1992  Lindsay et al. ..................... 250/306

OTHER PUBLICATIONS

Masai et al., "Scanning Tunneling: Microscopic Immunoassay: A Preliminary Experiment", J. Vacuum Sci. Technology, A8(1), (Jan./Feb. 1990), pp. 713–717.
Haussling et al., "Biotin Functionalized Self-Assembled Monolayers on Gold: Surface Plasmon Optical Studies of Specific Recognition Reactions", Langmuir: ACS J. Surfaces & Colloids, 7(9), (Sep. 1991), pp. 1837–1840.
Prime et al., "Self-Assembled Organic Monolayers: Model Systems for Studying Adsorption of Proteins at Surface", Science, 252, (May 24, 1991), pp. 1164–1167.
Evans et al., "Detachment of Agglutinin Bonded Red Blood Cells I: Forces to Rupture Molecular Point Attachments", Biophysical J., 59, (Apr. 1991), pp. 838–848.
Leckband et al., "Long Range Attraction and Molecular Rearrangements in Receptor-Ligand Interactions", Science, 255, (Mar. 13, 1992), pp. 1419–1421.
Helm et al., "Measurement of Ligand-Receptor Interactions", Biochemistry, 88, (Sep. 1991), pp. 8169–8173.
Ahlers et al., "Protein Interactions with Ordered Lipid Films: Specific and Unspecific Binding", Advanced Materials, 3, (1991), pp. 39–46.

Primary Examiner—Toni R. Scheiner
Assistant Examiner—Christopher L. Chi
Attorney, Agent, or Firm—Thomas E. McDonnell; John J. Karasek

[57] ABSTRACT

A sensor for ultra-low concentration chemical recognition comprises a force transducer, a tip coupled to this force transducer, and a substrate positioned for force interaction with the force transducer tip, where the substrate and tip are chemically modified with antigens, antibodies, nucleic acids, or chelating agents so that there is a specific force interaction between the tip and the substrate in the presence of the target species, and a measurably different force interaction in the absence of the target species.

18 Claims, 7 Drawing Sheets

SENSOR FOR ULTRA-LOW CONCENTRATION MOLECULAR RECOGNITION

BACKGROUND OF THE INVENTION

1. Field of the Invention

This invention relates to a sensor for measuring in real time a chemical species at ultra-low concentrations, even down to a single molecule.

2. Description of the Related Art

Chemical hazards, including hazards from biochemical substances, are a concern in an increasing number of arenas, including the modern battlefield (where the threat of chemical and biological warfare has returned), the workplace and the environment. Sensitive chemical sensors for detecting these hazards are needed. Chemical sensors with high sensitivity are also needed in other arenas, such as in the laboratory and on production lines, for conducting microtrace analysis, quality control, medical diagnostics, etc.

Such sensors should be highly selective, distinguishing between the species of interest and other species. The sensors should be reliable, not giving a significant number of false positives or false negatives. They should be adaptable to a wide variety of different species, and should be highly durable and transportable. They should operate in real-time. Most importantly, these sensors should be sensitive to extremely low concentrations, ideally being able to detect a single molecule of the target species.

One approach to ultra-low concentration detection is typified by Masai et al., *Scanning tunneling microscopic immunoassay: A preliminary experiment.*, J. Vacuum Sci. Tech. A8 (1) 713-17 (1990). In this approach, an antibody is attached to a conductive substrate. This antibody is selected for immune complexation (antigen-antibody complexation) with the target antigen. The analyte solution, with the target antigen, is incubated with the treated substrate to form immune complexes on the substrate surface. The substrate is treated a second time with the antibody, to "sandwich" the target antigen between two antibodies. The immune complexes are then decorated with gold colloidal particles (gold with bioactive coatings), and these gold colloids are imaged by scanning tunneling microscopy (STM) or some other method.

This approach is very slow, entailing several incubation steps lasting several hours. This makes the process unsuitable for use in an alarm system.

This approach also entails scanning the substrate with the STM tip, looking for these gold colloidal particles. This reduces the reliability of the process. The reason for this difficulty is that these immune complexes have limited binding constants. The antigens of interest would spend most of their time in solution. Detecting a particular antigen would require the immune complex to be bound to a point on the substrate at the same time the tip was passing over the same point.

Another drawback to this method is that it is limited to high molecular weight species, because sandwiching the target species requires the target to be large enough to bind simultaneously to two sandwiching species.

SUMMARY OF THE INVENTION

Accordingly, it is an object of this invention to detect ultra-low concentrations, down to a single molecule, of a wide range of chemical species, with a wide range of molecular weights.

It is a further object of this invention to detect these ultra-low concentrations with high selectivity and reliability, in real time, with durable and transportable chemical sensors.

These and additional objects of the invention are accomplished by the structures and processes hereinafter described.

The present invention is a chemical sensor comprising a force transducer, a tip coupled to the force transducer, and a substrate positioned for force interaction with the force transducer tip. The substrate and the tip are chemically modified so that there is a specific force interaction between the tip and the substrate in the presence of the target species, and a measurably different force interaction in the absence of the target species. Chemical modifiers are defined herein as molecules attached to the tip and/or the substrate to produce this force interaction.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

All the preferred embodiments of this invention use an atomic force microscope (AFM) 22 to measure the forces between the substrate 14 and the tip 12. The principal component of an AFM is a small cantilever which measures the force between a tip 12 attached to the cantilever and the substrate of interest 14. The force is determined by multiplying the measured cantilever deflection by the known spring constant of the cantilever. See generally Binning et al., *Atomic Force Microscope*, Physics Rev. Letters 56, 930 (1986); Murday et al., *Proximal Probes: Techniques for Measuring at the Nanometer Scale*, Materials Sci. & Eng'g B6, 77 (1990), incorporated by reference herein.

In this invention, both the AFM tip 12 and the substrate 14 are chemically modified so that there is a baseline force between the modified tip 12 and substrate 14 in the absence of the target species 20, and a measurably different force between the tip 12 and the substrate 14 in the presence of the species, due to interaction of the target species 20 with chemical modifiers 16,18 on the tip 12 and/or the substrate 14. This interaction may be in the form of a covalent bond, a Van der Waals interaction, an ionic interaction, recognition and binding events (which include chelation, immune complexation and binding of complementary nucleic acids), or other type of interaction. The specific type of interaction will be determined by the target species 20 and by the type of chemical modification to the tip 12 and the substrate 14.

Figure 1:
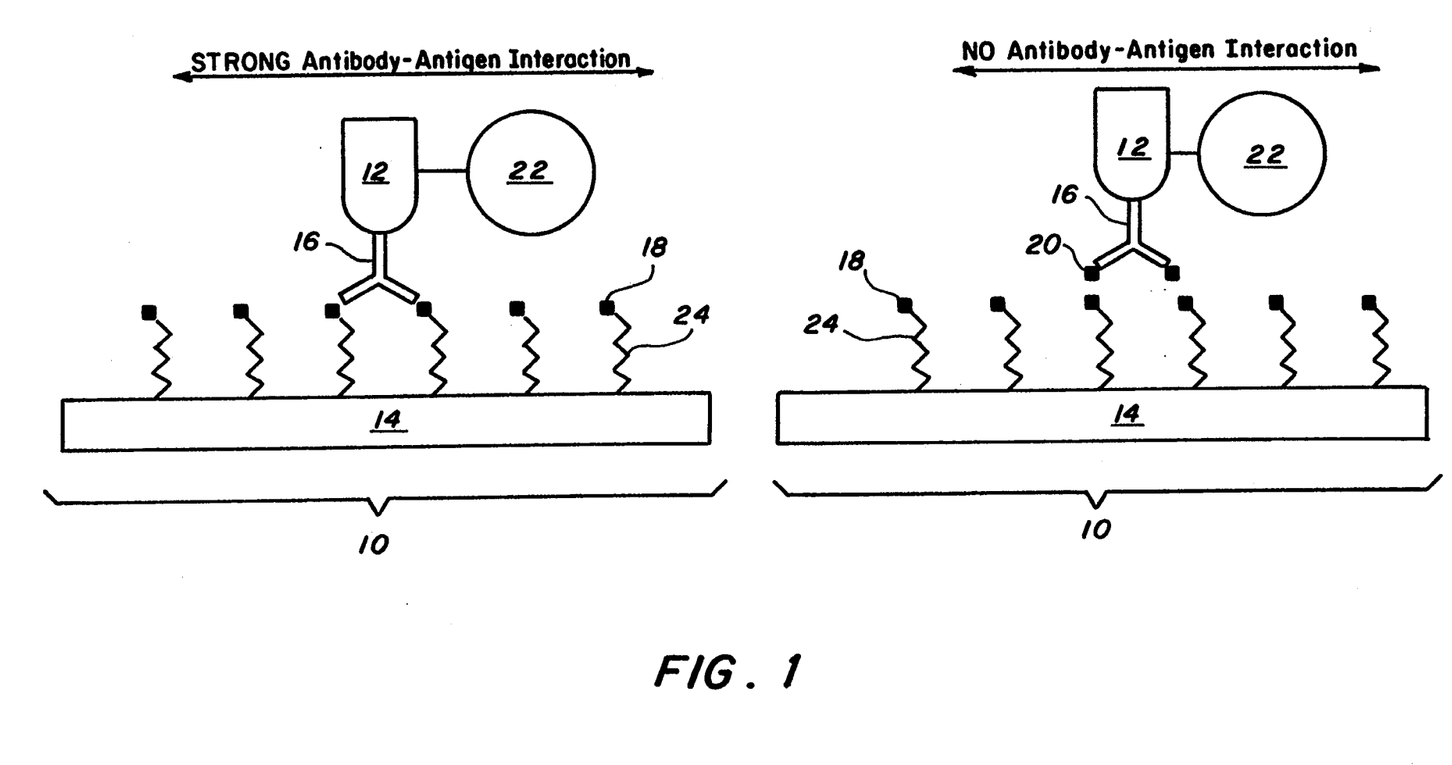
FIG. 1 shows an embodiment for detecting an antigen, where the antigen of interest is attached to the substrate and the appropriate antibody is attached to the tip.
Figure 2:
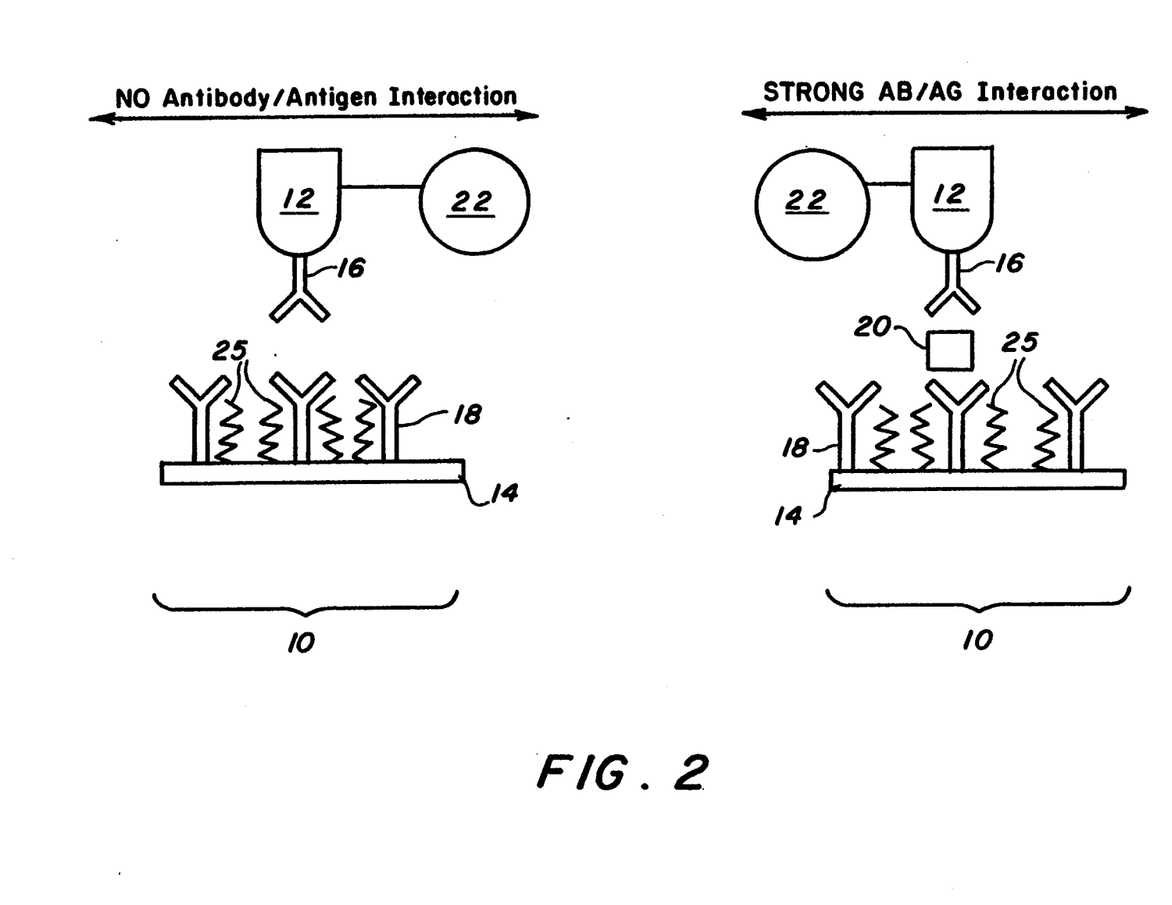
FIG. 2 shows an embodiment for detecting an antigen, where the appropriate antibody is attached to both the substrate and the tip.

A paradigm example of this occurs when the target species 20 is an antigen. For example, as shown in FIG. 1, an appropriate antibody 16 can be attached to the tip 12, and the antigen 18 can be attached to the substrate 14. When the tip 12 is brought in close proximity to the substrate 14 (typically less than 25 nm from the substrate and preferably less than 10 nm from the substrate), there is a very strong attraction between the tip 12 and the substrate 14. When a molecule of the target antigen 20 is interposed between the tip 12 and the substrate (by complexing with the antibody 16 on the tip 12 or otherwise), this strong attraction will decrease by several orders of magnitude. Thus, by monitoring the force between the tip 12 and the substrate 14, one can test in real time for the presence of the target species Likewise, as shown in FIG. 2, appropriate antibodies can be attached to both the tip 12 and the substrate 14. When the tip 12 is brought in close proximity to the substrate 14 (again, typically less than 25 nm from the substrate and preferably less than 10 nm from the substrate), there is a weak attraction between the tip 12 and the substrate 14. Possibly, there is even (depending on the tip-to-substrate separation and the medium in which the tip and the substrate are immersed) a small repulsion between the tip 12 and the substrate 14. However, when a molecule of the target antigen 20 is interposed between the tip 12 and the substrate 14, this weak attraction will likewise increase by several orders of magnitude.

In the embodiment of the invention shown in FIG. 2, there is a small probability of a false negative signal. If two antigens 20 bind simultaneously to both the tip 12 and the substrate 14, the measured force is expected to change, but not as significantly as when there is one antigen 20 attached. For this reason, the embodiment of the invention shown in FIG. 1 is preferred over the embodiment shown in FIG. 2. However, because of the low concentrations of the target species 20 and the fact that the antigen/antibody complexes are in equilibrium with the ambient environment, it is not expected that the simultaneous binding of two antigens 20 will lead to significant errors.

Figure 3:
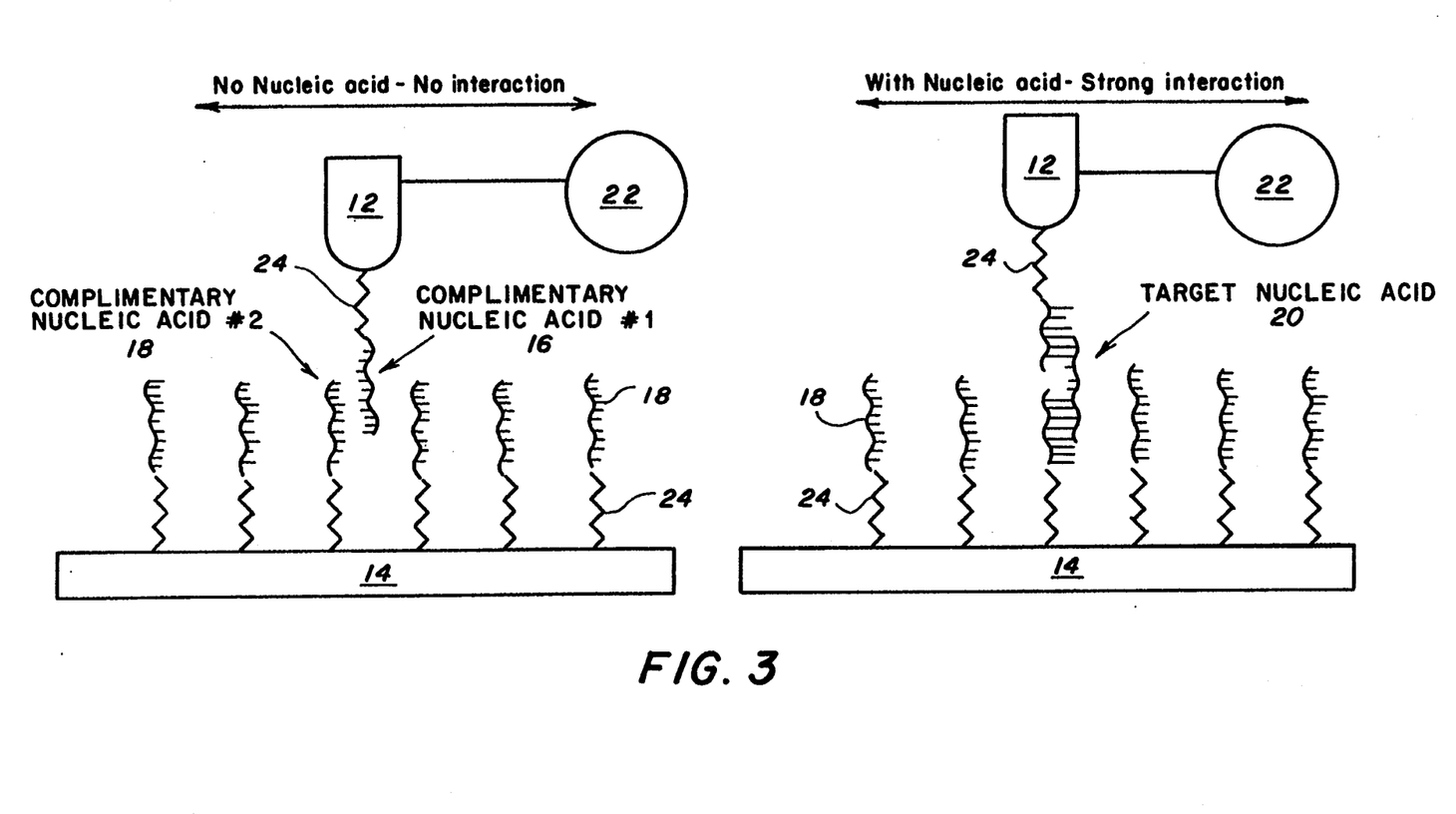
FIG. 3 shows an embodiment for detecting a nucleic acid, where complementary nucleic acids are attached to both the substrate and the tip.

Another paradigm example of the specific interaction of the target species 20 with chemical modifiers 16,18 on the tip 12 and/or the substrate 14 occurs when the target species 20 is a nucleic acid. For example, as shown in FIG. 3, a complementary nucleic acid 16 can be attached to the tip 12, and another complementary nucleic acid 18 can be attached to the substrate 14. When the tip 12 is brought in close proximity to the substrate 14 (again, typically less than 25 nm from the substrate and preferably less than 10 nm from the substrate), there is a weak attraction between the tip 12 and the substrate 14. Possibly, there is even (again depending on the tip-to-substrate separation and the medium in which the tip and the substrate are immersed) a small repulsion between the tip 12 and the substrate 14. However, when a molecule of the target nucleic acid 10 is interposed between the tip 12 and the substrate 14, this weak attraction will likewise increase by several orders of magnitude.

This invention is not limited to detecting bioactive species. Any target species can be detected by the present invention, so long as the AFM tip 12 and the substrate 14 can be chemically modified so that there is a baseline force interaction between the tip 12 and the substrate 14 in the absence of the target species 20, and there is a specific, measurable change in this force interaction in the presence of the target species 20.

Figure 4:
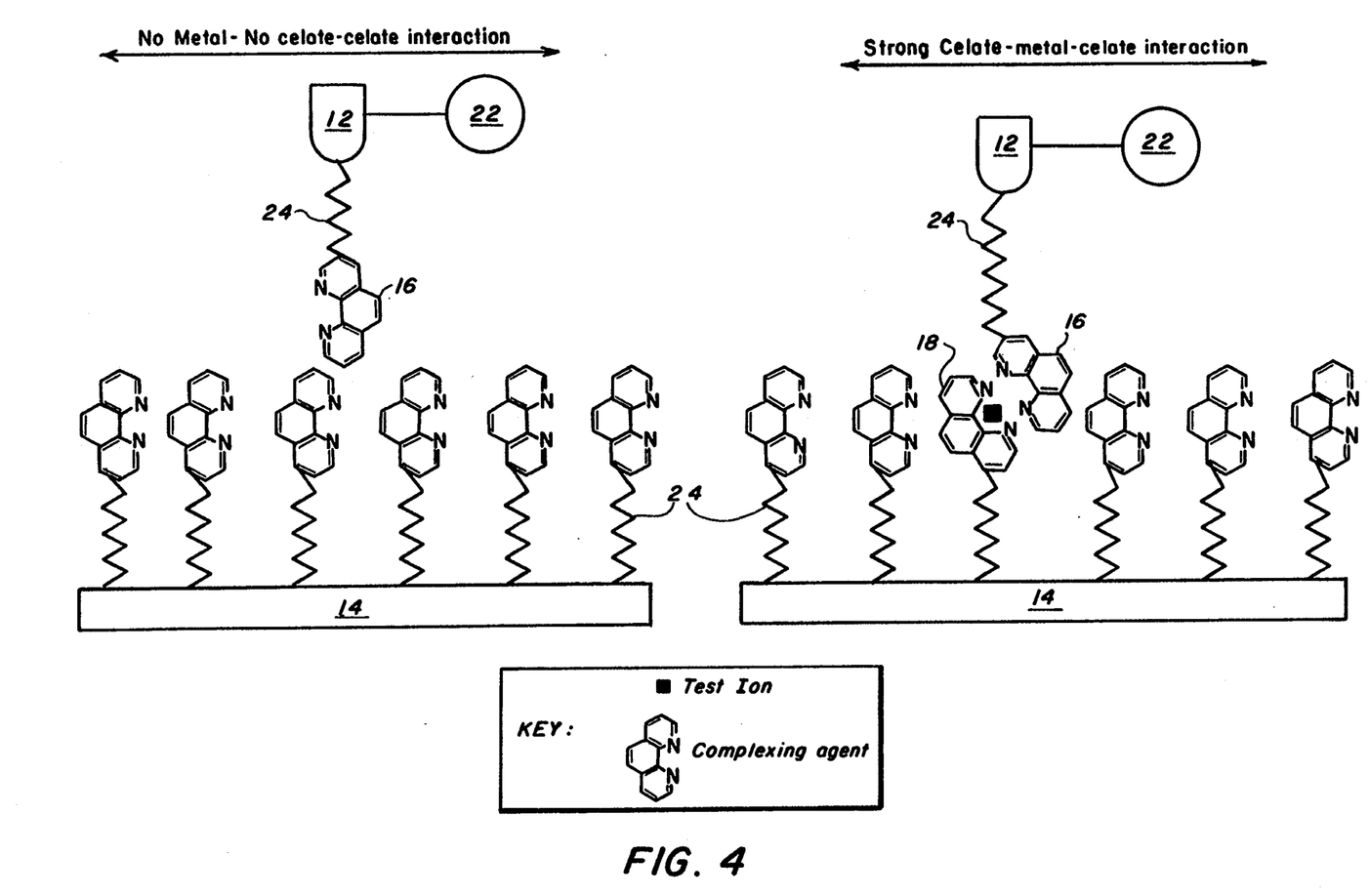
FIG. 4 shows an embodiment for detecting a metal ion, where chelating agents are attached to both the tip and the substrate.

For example, as shown in FIG. 4, the tip 12 and the substrate 14 can be modified by attaching a chelating agent 16,18 (shown here as 1,10-Phenanthroline). Other chelating agents will work, including other aromatic heterocyclic bases such as 2,2'-bipyridyl. The force interaction between the tip 12 and the substrate 14 is different by several orders of magnitude when, for example, iron 20 is interposed between the tip 12 and the substrate 14. The magnitude of this change is specific to iron.

As shown in Table 1, complexes of different metals have different stability constants. Consequently, different changes are observed in the presence of other species (e.g. chromium, nickel, etc.).

In this embodiment of the invention, the target species is a multidentate ligand. In this embodiment of the invention, the chelating agent 16,18 preferably is one that will not completely chelate the target species 20 with a single chelating molecule. In other words, the chelating agent preferably is one where the target species 20 is sandwiched by chemical modifiers 16,18 on the tip 12 and the substrate 14. Typically, the target species 20 binds simultaneously to exactly two chelating molecules 16,18. Although tridentate chelating complexes may also be used, they are less preferred, because having three chelating agents bind to the metal will probably require a higher effective concentration of chemical modifiers on the substrate than is preferred (as explained below).

This invention has the additional feature of performing quantitative analysis. To perform this type of analysis, the force interaction between the tip 12 and the substrate 14 is monitored for time $t_{Total}$. During this time, the measured force will vary intermittently between the baseline force $F_{baseline}$ and the measurably different force $F_{target}$ that is specific to the interaction of the target molecule 20 with the sensor 10. The concentration of the target species 20 is then determined by comparing the amount of time ($t_{Ftarget}$) the measured force is at the level associated with the target species 20 to $t_{Total}$. This ratio will vary with the target species concentration, according to the relationship:

$$[\text{Target}] \propto \frac{t_{Ftarget}}{t_{Total}}$$

where [Target] is the concentration of the target species 20 in the analyte.

The reason for this fluctuation in the measured force is that an equilibrium exists for these target molecules 20 between being bound to the chemical modifiers 16,18 on the sensor and being free in the ambient solution. In low concentrations, the ambient target molecules 20 spend most of their time in solution. As the concentration of the target 20 in solution increases, the fraction of time that the target molecules 20 are bound to the chemical modifiers 16,18 on the sensor also increases. Consequently, the fraction of time that the measured force is at the level associated with the target species 20 will also increase.

Figure 7:
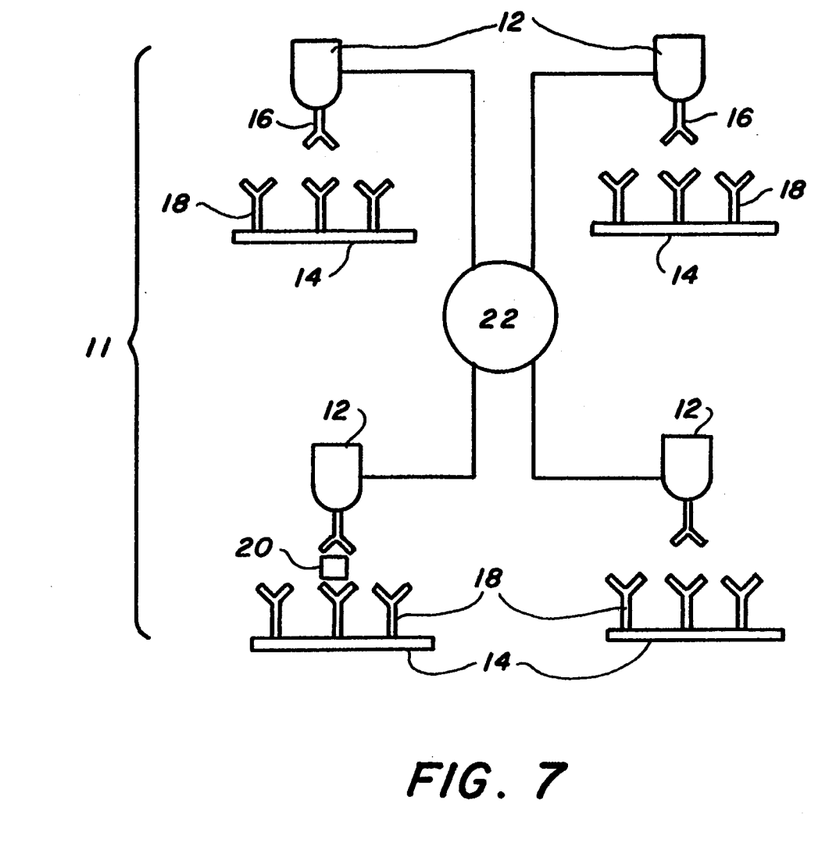
FIG. 7 shows an array of modified tips and substrates, where the tips are coupled to a common means for measuring the force interaction.

Another feature of this invention is that these sensors can be bundled together in arrays 11, as shown in FIG. 7. Multiple AFM tips 12 with their associated substrates 14 can be connected in parallel to a single AFM 22. This embodiment gives the sensor a great deal of redundancy, and consequently improves the durability of the system. If a single tip 12 should fail in this embodiment, the system will still operate.

There are other advantages to bundling these tips 12 together in arrays 11. For example, by bundling together a large number of tips 12 in parallel, instantaneous concentration data can be collected. This embodiment eliminates the need for the time averaging referred to above. In this embodiment of the invention, at any given time the fraction of tips 12 measuring a force equal to the force level associated with the target species 20 will be proportional to the concentration of the target species 20.

Another advantage to building arrays 11 of these tips 12 is that multiple species can be tested for simultaneously. By configuring each tip 12 in an array 11 to test for a different species, it is possible to test for a plurality of species.

At present, AFM tips connected in parallel with a high packing density (micrometer to nanometer scale separation between tips) are not individually addressable. Consequently, arrays for instantaneous concentration data or data on multiple species can currently only be fabricated with the sensors separated by millimeter-scale distances. As AFM technology improves, however, it is anticipated that arrays with high packing densities with individually addressable tips may be fabricated for measuring concentrations instantaneously and for testing for multiple species instantaneously.

In a preferred embodiment of the invention, the chemical nature of the substrate 14 is controlled to reduce contamination when sampling hostile environments. In this context, a hostile environment is an environment with contaminants which may be adsorbed onto the substrate 14, potentially interfering with the sensor. Therefore, it is preferred to control the chemical nature of the substrate 14 by attaching molecules of selected chemical nature 25. This will limit adsorption of contaminants from the environment onto the substrate. For example, by mixing long-chain alkyl thiols 25 with the chemical modifiers 18 attached to the substrate 14 (which may be, as stated above, antigens, antibodies, chelating agents, or some other chemical modifiers), a hydrophobic surface can be prepared, suitable for use in nonpolar solutions. Conversely, polyethylene oxide thiols 25 can be used to prepare hydrophilic surfaces, suitable for use in aqueous solutions. See generally Prime & Whitesides, *Self-Assembled Organic Monolayers: Model Systems for Studying Adsorption of Proteins at Surfaces*, Science 252, 1164 (1991), incorporated by reference herein.

In a preferred embodiment of the invention, the chemical modifiers 18 are attached to the substrate 14 via long linker arms 24. In this context, long linker arms 24 are between five and 300 carbons in length. Preferably, polyethylene oxide linker arms of less than 20 atoms in length are used to provide spacing between the chemical modifiers and the substrate, thereby reducing steric interactions with the surface.

Figure 5:
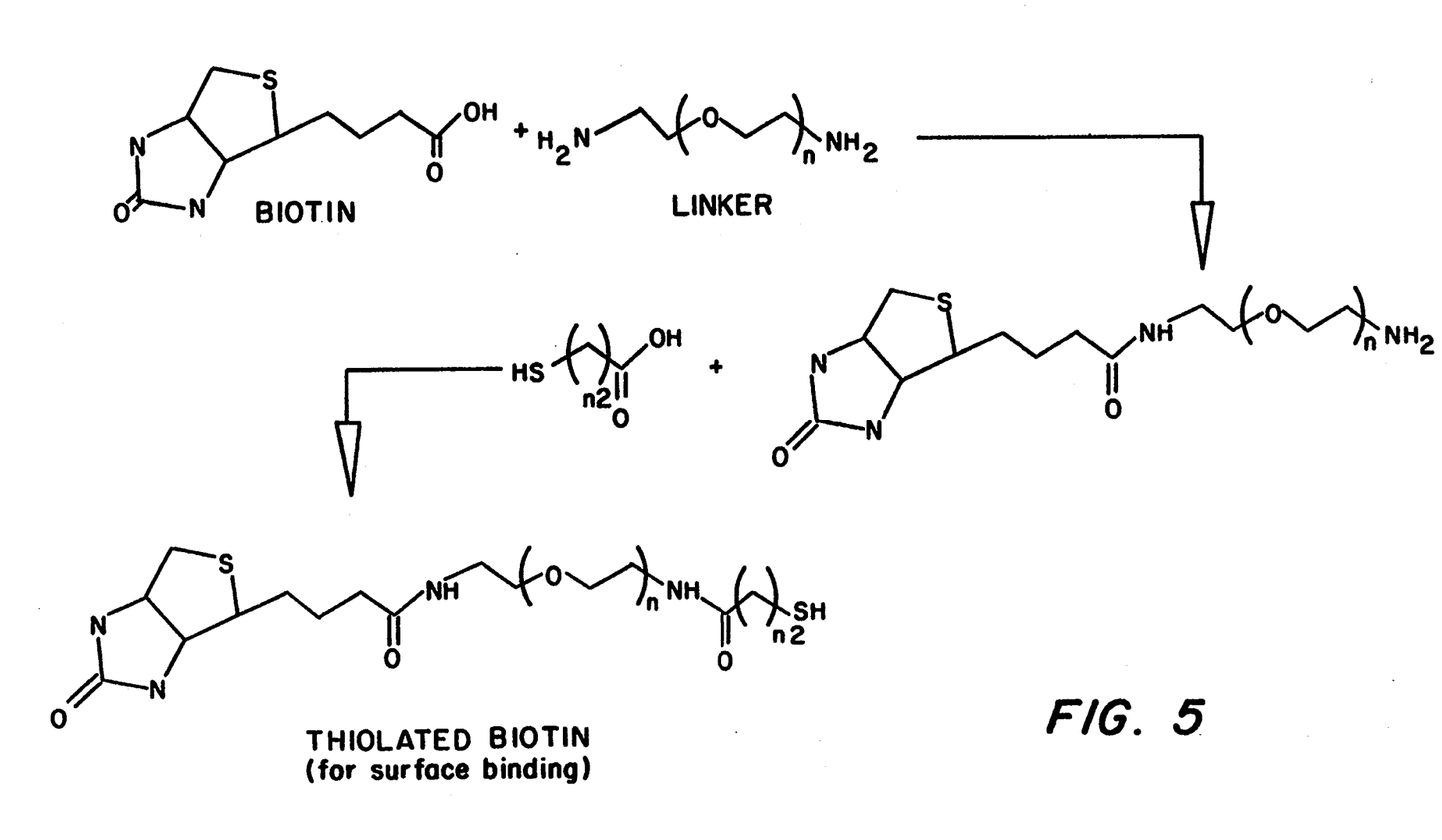
FIG. 5 shows chemical reactions useful for attaching chemical modifiers to silicon (amino-terminated linker) or gold (thiol-terminated linker) substrates.
Figure 6:
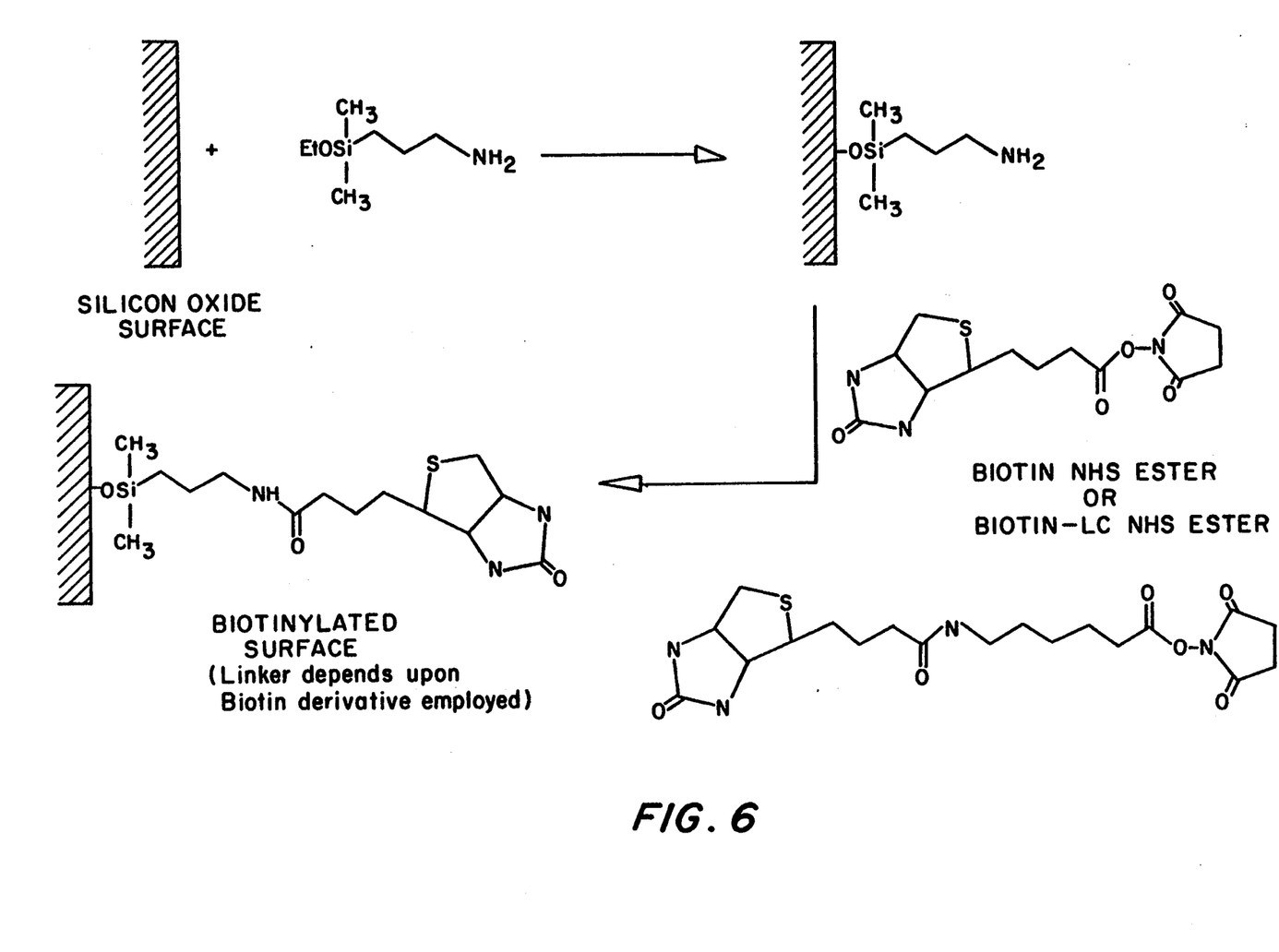
FIG. 6 shows chemical reactions useful for attaching chemical modifiers to silicon oxide substrates.

In a preferred embodiment of the invention, the long linker arms 24 are modified to improve binding to the substrate 14. When a silicon substrate 14 is used, it is preferred to terminate the long linker arms 24 with amino groups for attachment to the antigen. When a gold substrate 14 is used, it is preferred to terminate the long linker arms 24 with thiol groups for attachment to the substrate. FIG. 5 shows preferred reactions for modifying the linker arms for attachment to silicon and gold substrates. When a silicon oxide substrate 14 is used, it is preferred to terminate the long linker arms 24 with EtOSi groups. FIG. 6 shows preferred reactions for attaching chemical modifiers to a silicon oxide substrate.

In a preferred embodiment of the invention, the effective concentration of the chemical modifiers 18 on the substrate 14 is kept low; preferably less than 10% of the species attached to the substrate 14 are chemical modifiers 18. Most preferably about 1% of the species attached to the substrate are chemical modifiers In this context, effective concentration means an area density of these chemical modifiers 18 on the substrate 14 where the probability of one of these chemical modifiers 18 interacting with the modified tip is equal to the probability of an ambient target species 20 interacting with the modified tip 12. Area density is defined as the percentage of the substrate area occupied by chemical modifiers. An advantage to a low effective concentration of modifiers on the substrate is that steric interference on the substrate is reduced. A further advantage is that the sensitivity of the sensor is improved. The latter advantage is due to the competition between the modified substrate and the ambient target species to interact with the chemical modifiers 16 on the tip 12. If the effective concentration of the modifiers 18 on the substrate 14 is too high, the substrate dominates this competition and sensitivity suffers.

In a preferred embodiment of the invention, any chemical modifiers 16,18 with discrete binding sites are attached with orientation for maximum exposure of these binding sites (i.e. with directionality). For instance, antibodies typically have a plurality of binding sites for binding to their corresponding antigens. It is preferred to not attach these antibodies at or near the binding sites. Therefore, in a preferred embodiment of the invention, oriented antibodies 16,18 are attached to the substrate 14 and/or tip 12 using standard techniques for oriented attachment. These standard techniques include use of a protein A surface, carbohydrate-hydrazine coupling (see *Affi-Gele* ® *Hz Immunoaffinity Kit*, Bio-Rad Bulletin 1424 (1988), Bio-Rad Laboratories, Richmond, Calif., and FAB fragment-thiol coupling. Most preferably, antibodies are oriented by the use of FAB fragment-thiol coupling.

Having described the invention, the following examples are given to illustrate specific applications of the invention, including the best mode now known to perform the invention. These specific examples are not intended to limit the scope of the invention described in this application.

EXAMPLES

Example 1

Detection of Biotin in a Sensor Having a Substrate Modified with Biotin and a Tip Modified with Streptavidin As shown in FIG. 5, biotin 18 is modified by attachment of a polyethylene oxide linker arm 24. The amino biotin is reacted with $HSCH_2COOH$ or $HS(CH_2)_{11}COOH$ to form thiolated biotin. The thiolated biotin is attached to a gold substrate 14. Alkyl thiols 25 are then attached to vacant sites on the substrate 14, to make the substrate hydrophobic.

Streptavidin 16 is attached to the tip 12 by FAB fragment-thiol coupling. The modified tip 12 is positioned about 10 nm from the modified substrate 14, resulting in a strong attractive force. It is anticipated that introducing ambient biotin 20 results in a reduction of this strong binding force by four orders of magnitude, due to this ambient biotin 20 binding to the receptor sites on the streptavidin antibody 16.

Example 2

Detection of Biotin in a Sensor Having a Substrate and a Tip Modified with Streptavidin The tip 12 is prepared as in Example 1. Streptavidin 18 is attached to the substrate 14 by FAB fragment-thiol coupling. Alkyl thiols 25 are then attached to vacant sites on the substrate 14, to make the substrate hydrophobic. The modified tip 12 is positioned about 10 nm from the modified substrate 14, resulting in a weak attractive force. It is anticipated that introducing ambient biotin 20 results in an increase of this weak binding force by four orders of magnitude, due to this ambient biotin 20 binding to the receptor sites on the streptavidin antibody 16.

Obviously, many modifications and variations of the present invention are possible in light of the above teachings. It is therefore to be understood that, within the scope of the appended claims, the invention may be practiced otherwise than as specifically described.

TABLE 1

Stability Constants for Selected 1,10-Phenanthroline Complexes in Water

| Ion | Log $K_1$ | Log $K_2$ | Log $K_3$ |
|---|---|---|---|
| $Cd^{+2}$ | 5.78 | 5.04 | 4.10 |
| $Co^{+2}$ | 7.25 | 6.70 | 5.95 |
| $Cu^{+2}$ | 9.25 | 6.75 | 5.35 |
| $Fe^{+3}$ | 6.5 | 4.9 | 12.12 |
| $Fe^{+2}$ | $K_1K_2 < K_3$ Total = 21.3 | | |

From: K. Burger, Organic reagens in Metal Analysis, Pergamon Press, New York, 1973, p. 226.

What is claimed is:

1. A sensor for a selected target molecule, comprising:
  a.) a tip which has been chemically modified by attachment of chemical modifiers selected from the group consisting of antigens, antibodies, nucleic acids, and chelating agents,
  b.) a substrate positioned for force interaction with said tip, wherein said substrate has been chemically modified by attachment of chemical modifiers selected from the group consisting of antigens, antibodies, nucleic acids, and chelating agents, to produce a specific force interaction between said chemically modified tip and said chemically modified substrate in the presence of said target molecule as chemical modifiers on said tip and/or substrate bind to said target molecule, and a measurably different force interaction between said chemically modified tip and said chemically modified substrate in the absence of said target molecule, and
  c.) an atomic force transducer, coupled to said tip, for measuring said force interaction between said substrate and said tip.

2. The sensor of claim 1, wherein the selected target molecule is an antigen, wherein said chemical modification of said substrate comprises attaching said antigen to said substrate, and wherein said chemical modification of said tip comprises attaching to said tip an antibody capable of forming an immune complex with said target molecule antigen in the presence of said target molecule antigen, and wherein said antibody is also capable of forming an immune complex with said substrate-attached antigen in the absence of said target antigen.

3. The sensor of claim 1, wherein the selected target molecule is an antigen, wherein said chemical modification of said substrate and said tip comprises attaching to said substrate and said tip an antibody capable of forming an immune complex with said antigen.

4. A plurality of the sensors of claim 1, wherein said tips are connected in parallel to a common means for measuring said force interaction, to form an array.

5. The sensor of claim 1, wherein said tip is an atomic force microscope tip.

6. The sensor of claim 1, wherein said substrate is positioned between about 5 nm and about 10 nm from said tip.

7. The sensor of claim 1, wherein said chemical modifiers attached to said substrate are attached to said substrate with linker arms.

8. The sensor of claim 7, wherein said linker arms are polyethylene oxide linker arms.

9. The sensor of claim 1, wherein said modified substrate is hydrophobic.

10. The sensor of claim 1, wherein said modified substrate is hydrophilic.

11. The sensor of claim 1, wherein said substrate is further chemically modified by attachment of a substance which limits adsorption of contaminants onto said substrate.

12. The sensor of claim 1, wherein said chemical modifiers are attached by FAB fragment-thiol coupling.

13. The sensor of claim 1, wherein the selected target molecule is a multidentate ligand and wherein said chemical modification of said tip and said substrate comprises attaching a chelating agent to said substrate and to said tip.

14. The sensor of claim 13, wherein said chelating agent does not completely chelate the target molecule with a single chelating molecule.

15. The sensor of claim 14, wherein said chelating agent is an aromatic heterocyclic base.

16. The sensor of claim 14, wherein said chelating agent is 1,10-Phenanthroline or 2,2'-bipyridyl.

17. The sensor of claim 1, wherein the selected target molecule is a nucleic acid, wherein said chemical modification of said substrate comprises attaching to said substrate a nucleic acid complementary to the target molecule, and wherein said chemical modification of said tip comprises attaching to said tip a nucleic acid complementary to the target molecule.

18. The sensor of claim 1, wherein said chemical modifiers with discrete binding sites are attached by FAB fragment-thiol coupling to said tip.

* * * * *